United States Patent [19]

Corbett

[11] Patent Number: 4,986,660
[45] Date of Patent: Jan. 22, 1991

[54] STOCK CONSISTENCY TRANSMITTER

[75] Inventor: James O. Corbett, Eustis, Fla.

[73] Assignee: The Electron Machine Corporation, Umatilla, Fla.

[21] Appl. No.: 341,711

[22] Filed: Apr. 21, 1989

[51] Int. Cl.$^5$ ............................................ G01N 21/00
[52] U.S. Cl. ..................................... 356/342; 356/343
[58] Field of Search ............... 356/336, 338, 343, 342, 356/442, 28

[56] References Cited

U.S. PATENT DOCUMENTS

| 3,714,444 | 1/1973 | Carr et al. | 356/442 |
|---|---|---|---|
| 3,930,726 | 1/1976 | Dolive | 356/39 |
| 3,994,602 | 11/1976 | Howarth | 356/343 |
| 4,078,863 | 3/1978 | Eriksson et al. | 356/104 |
| 4,110,044 | 8/1978 | Pettersson et al. | 356/103 |
| 4,577,963 | 3/1986 | Traina | 356/28.5 |
| 4,607,955 | 8/1986 | Corbett | 356/342 |
| 4,641,969 | 2/1987 | Lundberg et al. | 356/343 |
| 4,677,846 | 7/1987 | Lundberg | 73/63 |

FOREIGN PATENT DOCUMENTS 213510  9/1984  Fed. Rep. of Germany ...... 356/343

OTHER PUBLICATIONS

Waller, M. H., Measurement and Control of Paper Stock Consistency, Instrument Society of America, 1983, pp. 23-24, 35.

Primary Examiner—Richard A. Rosenberger
Attorney, Agent, or Firm—Shlesinger & Myers

[57] ABSTRACT

An apparatus for determining the amount of particle suspension in a fluid by measuring radiation reflection on the particles, comprises a beam of radiation directed into the fluid; first and second photovoltaic detectors for picking up at least a portion of the beam of radiation reflected from the particle suspension in the fluid; and a circuit for comparing the output of the first detector relative to the output of the second detector to obtain the amount of particle suspension in the fluid. The detectors are positioned such that the output of the first detector increases relative to the output of the second detector as the amount of particle suspension in the fluid increases.

29 Claims, 5 Drawing Sheets

STOCK CONSISTENCY TRANSMITTER

FIELD OF THE INVENTION

The present invention pertains generally to electro-optical devices using the backscattered light principle for measuring the consistency of a stock slurry containing wood fibers, and particularly to such devices having species compensation for different wood fibers.

BACKGROUND OF THE INVENTION

Paper making process requires the rapid and accurate measurement and control of consistency of the stock slurry during several stages in the process to ensure a uniform high-quality final product. Consistency, usually expressed in percentage, is defined as the weight in grams of oven-dry material in 100 grams of a pulp-water mixture. Prior art measurement devices have suffered from the problems of stock species and stock flow velocity, since different stock species and flow velocity produce errors in measuring stock consistency.

Different species of trees or other fiber sources exhibit fibers of differing lengths and diameters which are characteristic of their particular origin. The handling of the fiber during the paper making process further dimensionally alters the fiber from the degree of refining, type of process being used, mechanical, chemical, etc. Variations in fiber length and cross-section invariably cause an error in measurement—the direction and magnitude of the error being dependent on the measurement principle being used.

Instruments of a mechanical design utilizing shear as their principle of measurement typically exhibit a decrease in reading due to the apparent reduction in friction when measuring stock with short fiber length and small diameter, as would be found in the hardwood species. Conversely, softwood varieties with longer, larger fibers increase the apparent friction, thus increasing the reading for any given consistency.

Optical instruments employing backscatter as their principle of measurement generally exhibit an error in the reading in the opposite direction to that of the mechanical devices. Hardwood fiber, having a larger surface area for a given consistency than softwood fiber, causes the optical instrument's output to read higher due to the backscatter characteristics generally associated with an increase in consistency.

Velocity of the stock slurry also causes measurement error when one is attempting to gauge consistency. Usually, the measurement device cannot detect a difference between a changing flow rate or consistency, requiring that some compensation be made for the effects of flow velocity.

Therefore, there is a need for a consistency measurement device of the backscatter principle having the ability to compensate for variations in fiber size and stock flow velocity.

OBJECTS AND SUMMARY OF THE INVENTION

It is therefore an object of the present invention to provide a stock consistency transmitter which measures stock consistency accurately.

It is also an object of the present invention to provide a stock consistency transmitter which compensates for differing stock slurry species.

It is still an object of the present invention to provide a stock consistency transmitter which compensates for stock slurry flow velocity.

It is a further object of the present invention to provide a stock consistency transmitter which uses the optical backscatter principle with the ability to compensate for differing stock slurry species.

It is yet an object of the present invention to provide a stock consistency transmitter which uses the optical backscatter principle with the ability to compensate for stock slurry flow velocity.

It is an object of the present invention to provide a stock consistency transmitter which uses the optical backscatter principle with the ability to maintain constant the level of the light incident on reference detectors used in the present invention.

It is also an object of the present invention to provide a stock consistency transmitter which uses the optical backscatter principle with the ability to measure the stock slurry flow velocity.

It is a still further object of the present invention to provide a stock consistency transmitter which utilizes a microprocessor for mathematical operation and display of the signal from the transmitter.

It is a further object of the present invention to provide a stock consistency transmitter which is compact.

It is yet an object of the present invention to provide a stock consistency transmitter which can be used in many processes which contain a reflective or light dispersing suspension.

In summary, the present invention discloses an apparatus for measuring the amount of particle suspension in a fluid by measuring radiation reflection on the particles. The apparatus comprises means for producing a beam of radiation having at least first and second reflected portions; means for directing the beam of radiation into the fluid; first and second detector means for picking up at least the first and second portions, respectively, of the beam of radiation reflected from the particle suspension in the fluid; means for positioning the first and second detector means for permitting the output of the first detector means to increase relative to the output of the second detector means as the amount of particle suspension in the fluid increases; and means for comparing the output of the first detector means relative to the output of the second detector means to obtain the amount of particle suspension in the fluid. The beam has sufficient power so as to penetrate the fluid a sufficient distance to cause at least the first and second reflected portions of the beam to reflect from the particle suspension and impinge on the first and second detectors, respectively, at low amount of particle suspension.

DETAILED DESCRIPTION OF THE INVENTION

FIGS. 1, 2, 3 AND 4

Figure 1:
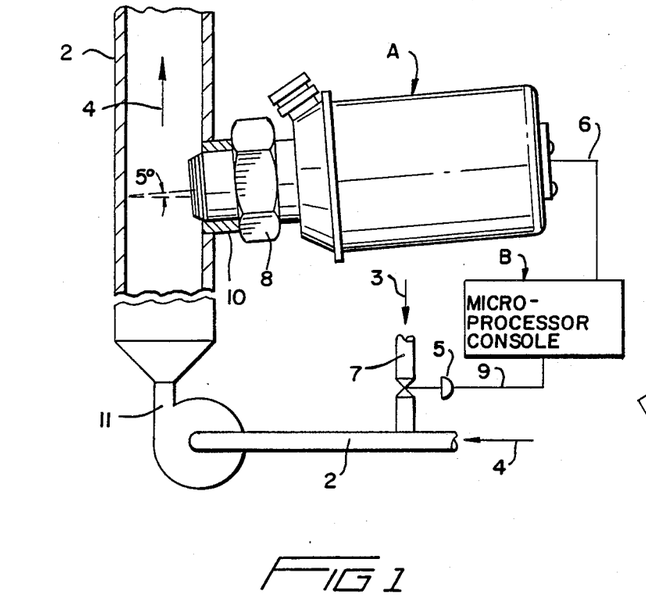
FIG. 1 is a fragmentary, partly schematic, partly cross-sectional view of a consistency control loop utilizing a stock consistency transmitter of the present invention.

A stock consistency transmitter A is connected to a pipe 2 for measuring the consistency of a stock slurry, generally indicated by the arrow 4, containing light reflecting fibers (not shown), as best shown in FIG. 1. The output of the transmitter A is fed to microprocessor console B by connection means 6 for numeric display of the measurement data and for other functions as will be described below. Dilution water, generally indicated by the arrow 3, is controlled by valve 5 disposed in dilution pipe 7 which is connected to the pipe 2. Connection means 9 preferably permits the microprocessor console B to control the operation of the valve 5 to maintain the desired consistency of the stock slurry 4. A centrifugal pump 11, disposed upstream of the transmitter A, advantageously helps insure uniform mixing of the dilution water 3 before the point of measurement for providing a representative of the entire cross-section of the pipe 2 to the transmitter A. The transmitter A is preferably connected to a vertical section of the pipe 2 and oriented at 5 degrees from the normal to the pipe 2, as best shown in FIG. 1. The vertical section of pipe 2 insures that the transmitter A is measuring across a full pipe for greater accuracy. The angular inclination of the transmitter A also insures greater accuracy of measurement, as discussed below. A nut 8 secures the transmitter A to pipe 2 by engaging to a short piece of pipe 10 which is welded to pipe 2.

Figure 2:
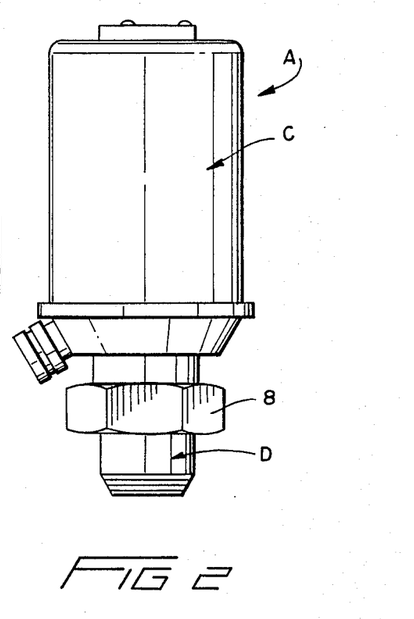
FIG. 2 is a side elevational view of a stock consistency transmitter of the present invention.
Figure 3:
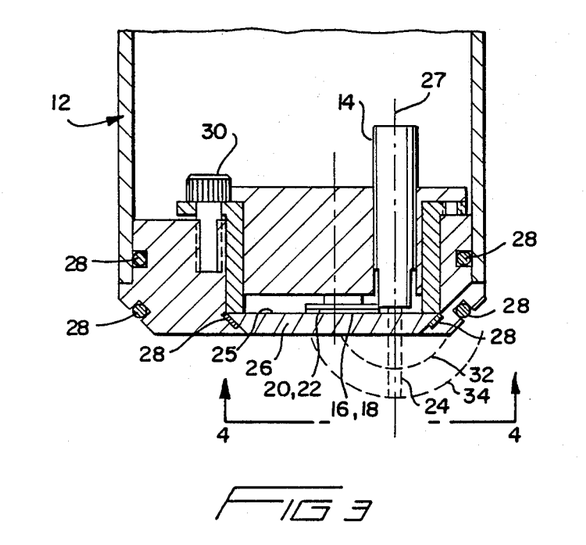
FIG. 3 is an enlarged, partly cross-sectional, fragmentary, side elevational view of an optical sensing portion of the present invention, taken from FIG. 2.
Figure 4:
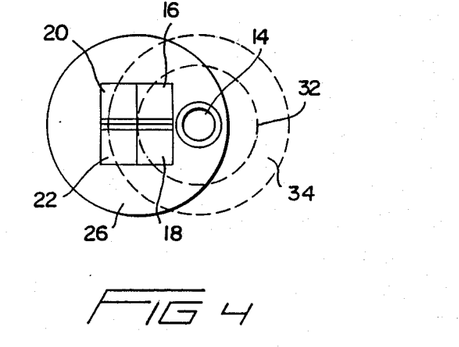
FIG. 4 is a fragmentary, schematic bottom view, taken from FIG. 3 along line 4—4, showing backscatter patterns substantially characteristic of high and low stock slurry consistencies, relative to the positions of photovoltaic detectors used in the present invention.

The transmitter A comprises an electrical circuitry portion C and an optical sensing portion D, as best shown in FIG. 2. Sensing portion D includes a housing 12 enclosing an incandescent lens-end lamp 14, reference photovoltaic detectors 16 and 18, and measure photovoltaic detectors 20 and 22, as best shown in FIGS. 3 and 4. Light beam 24 from the lamp 14 is directed through a sealed sapphire window 26 into the stock slurry 4. The light beam 24 includes an axis 27 which may be disposed at any angle relative to the direction of flow of the stock slurry 4. The detectors 16, 18, 20 and 22 are disposed adjacent an inner surface 25 of the window 26. The reference detectors 16 and 18 are disposed adjacent the lamp 14, while measure detectors 20 and 22 are disposed radially away therefrom. Since the stock slurry is normally abrasive, sapphire is advantageously used for window 26 for durability. The window 26 is preferably inclined at 5 degrees from the direction of flow of the stock slurry 4 to permit the moving stock slurry 4 to provide a wiping action on the window 26, thereby keeping the window 26 relatively clean and insuring accurate measurement for the transmitter A.

Sealing gaskets 28 provide a liquid-tight connection between the transmitter A and the pipe 2. Sealing gaskets 8 further provide sealing means for the window 26 with the housing 12. A plurality of retaining screws 30 (only one shown) hold the window 26 in place.

The detectors 16, 18, 20 and 22, disposed adjacent the inner surface of window 26, measure the varying quantity of reflected light which re-enters the window 26 from the stock slurry. The outputs of the detectors 16, 18, 20 and 22 are proportional to the amount of reflected light incident thereon. Reference detectors 16 and 18 are disposed adjacent the lamp 14, while measure detectors 20 and 22 are disposed away from the lamp 14. The detectors 16, 18, 20 and 22 and the window 26 are substantially transverse to the axis of the lamp 14 and the axis 27 of the light beam 24. The exact placement of the detectors 16, 18, 20 and 22 will depend on the range of consistencies of the stock slurry being measured. The arrangement shown in FIGS. 3 and 4 is preferable for stock consistencies between 1% and 5%.

Light reflected from the stock slurry will generally exhibit a range of backscatter patterns (reflected light), depending on the consistency of the stock slurry. The backscattered light from a stock slurry of a relatively high consistency will generally fall within an area 32 which encompasses the reference detectors 16 and 18. The backscattered light of a relatively low consistency will generally fall within an area 34, which includes the area 32 and encompasses measure detectors 20 and 22, and reference detectors 16 and 18, as best shown in FIGS. 3 and 4.

The light beam 24 is projected by the lens-end lamp 14. The light beam 24 must have enough power to penetrate the stock slurry 4 a sufficient distance at low consistencies so as to provide a portion of the light beam 24 to reflect from the stock slurry 4 and impinge on the detectors 16, 18, 20 and 22.

The detectors 16, 18, 20 and 22, generate voltage when backscattered light from the stock slurry impinges on them. The consistency measurement is obtained by measuring the differential voltage between the measurement detectors 20 and 22, and the reference detectors 16 and 18. The differential voltage of the reference detectors 16 and 18 relative to the measure detectors 20 and 22 increases with increasing consistency, since less light will be reflected on measure detectors 20 and 22 as on reference detectors 16 and 18 as the consistency increases. The reason is that stock of a low consistency, which contains less light reflecting fibers, is more easily penetrated with the light from lamp 14 than high consistency stock, which contains more light reflecting fiber. Therefore, the backscattered light for low consistency stock slurry has more uniform intensity over the larger area 34 than the backscattered light for high consistency stock slurry, which has greater intensity at the center of lamp 14 and rapidly diminishes with increases in radius.

In view of the above, the outputs of detectors 16, 18, 20 and 22 are more equally matched when measuring low consistency stock slurry than when measuring high consistency stock slurry. The outputs of measure detectors 20 and 22 decrease relative to the outputs of reference detectors 16 and 18 in non-linear proportion to the increase in consistency of the stock.

FIGS. 5 THROUGH 11

Figure 5:
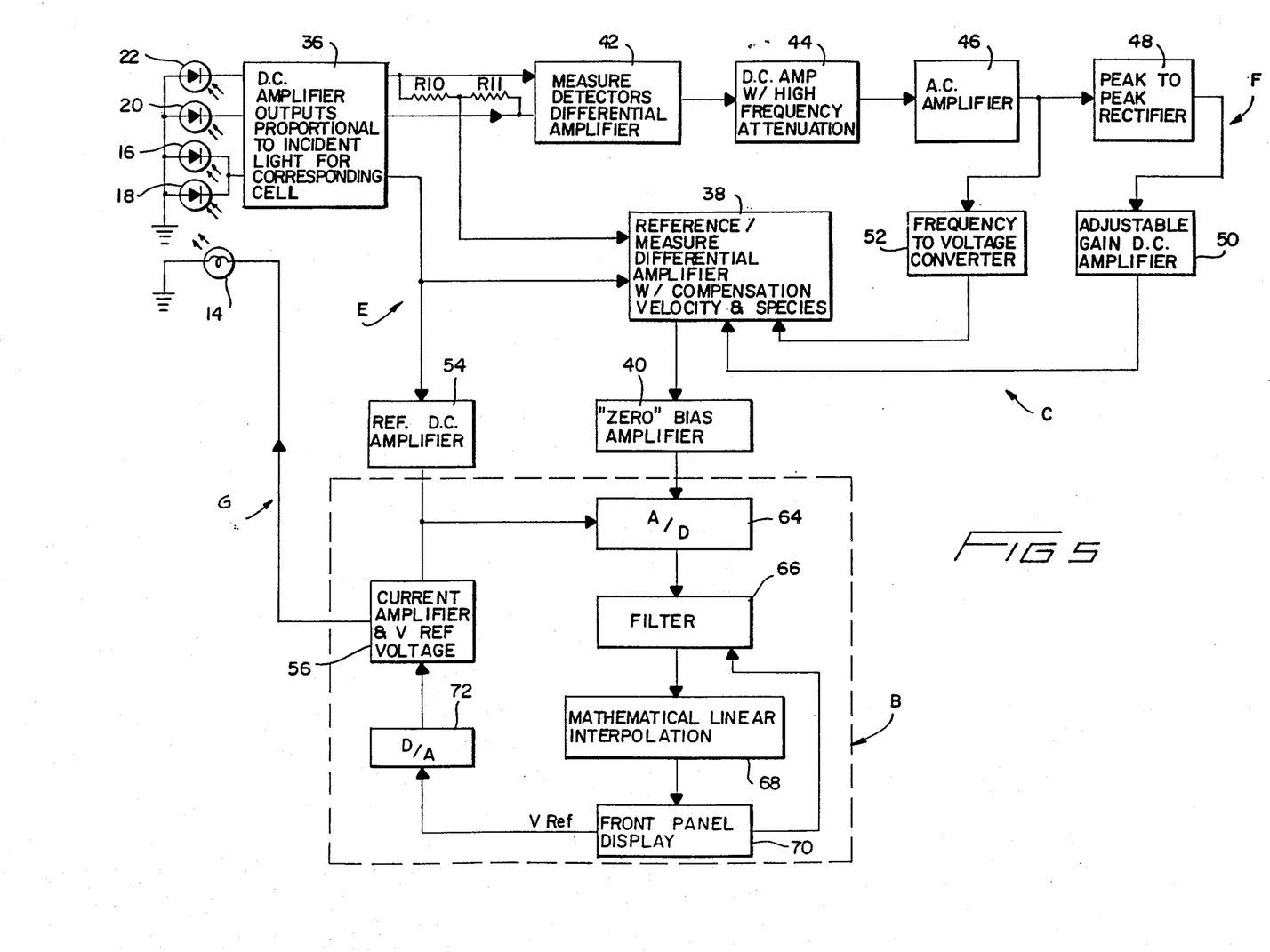
FIG. 5 is a functional electrical block diagram of the present invention.

The electrical portion C of transmitter A comprises a consistency measurement circuit E which includes circuit blocks 36, 38 and 40; compensation circuit F which includes circuit blocks 36, 42, 44, 46, 48, 50 and 52; and automatic gain control circuit G which includes circuit block 54 and circuit block 56 within microprocessor console B, as best shown in FIG. 5.

Figure 10:
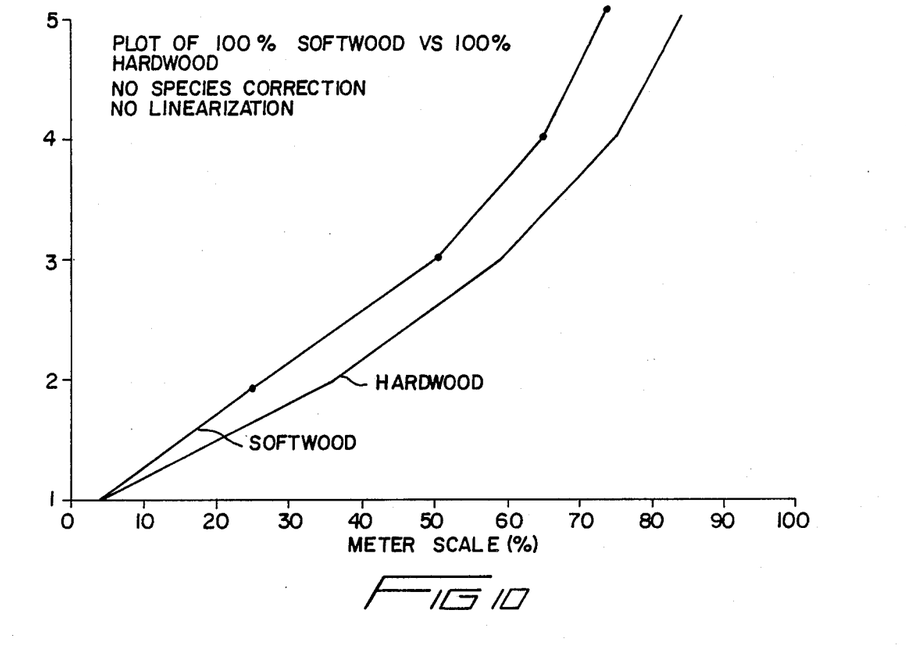
FIG. 10 is a graph output of the present invention for different consistencies of hardwood and softwood stock slurries relative to a meter scale, without species correction or linearization.
Figure 11:
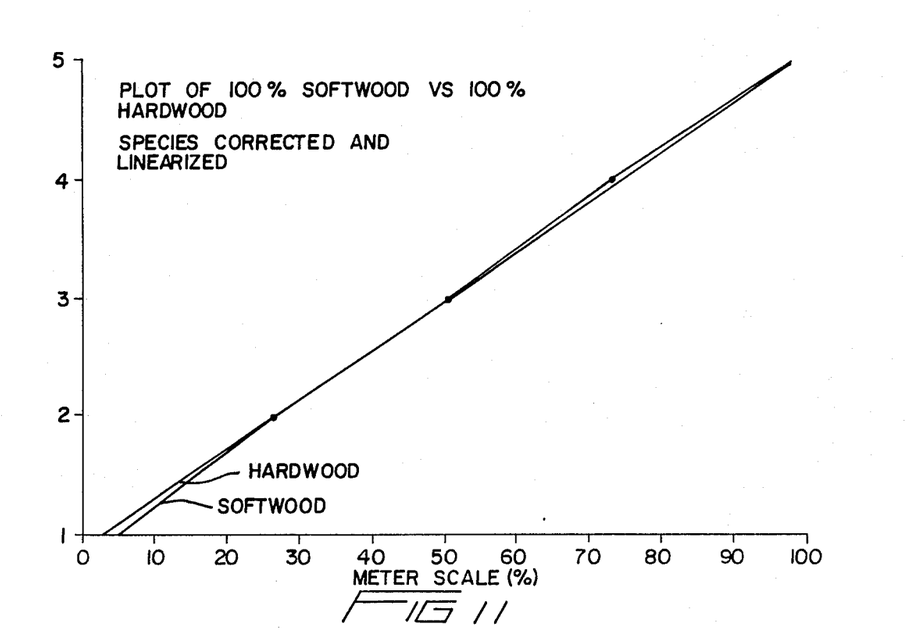
FIG. 11 is a graph output of the present invention for different consistencies of hardwood and softwood stock slurries, with species correction and linearization.

The output of measurement circuit E is fed to microprocessor console B. Since the output of measurement circuit E is not linear relative to a meter scale, as best shown in FIG. 10, microprocessor B performs linearization of the output to fit a desired slope for process control and for mathematical interpolation of the raw filtered data to obtain a desired output. The microprocessor console B also performs other functions such as providing multi-range capability for various spans, ranges, products, etc.,; providing temperature compensation where required by the application; providing high and low set points; etc.. Microprocessor console B includes analog/digital circuit block 64, filter circuit block 66, microprocessor 68, front panel display 70, digital/analog circuit block 72 and circuit block 56, as best shown in FIG. 5.

Circuit block 64 converts the analog signal from the measurement circuit E to digital signal for input to filter circuit block 66. Filter circuit block 66 allows the operator to average the output from measurement circuit E over various time periods to cause the output to be relatively "noise" in a noisy process. Front panel display 70 allows the user to adjust the response of filter circuit block 66 and to adjust the voltage reference for circuit block 56. Digital/analog circuit block 72 converts the voltage reference signal from digital to analog.

Front panel display 70 displays the output of transmitter A in numeric form and provides a means for the operator to communicate with the microprocessor 68 to change the response of filter circuit block 66, adjust the reference voltage for the automatic gain control circuit G, as will be discussed below, calibrate the transmitter A, test diagnostic features, etc..

CIRCUIT BLOCK 36

Figure 6:
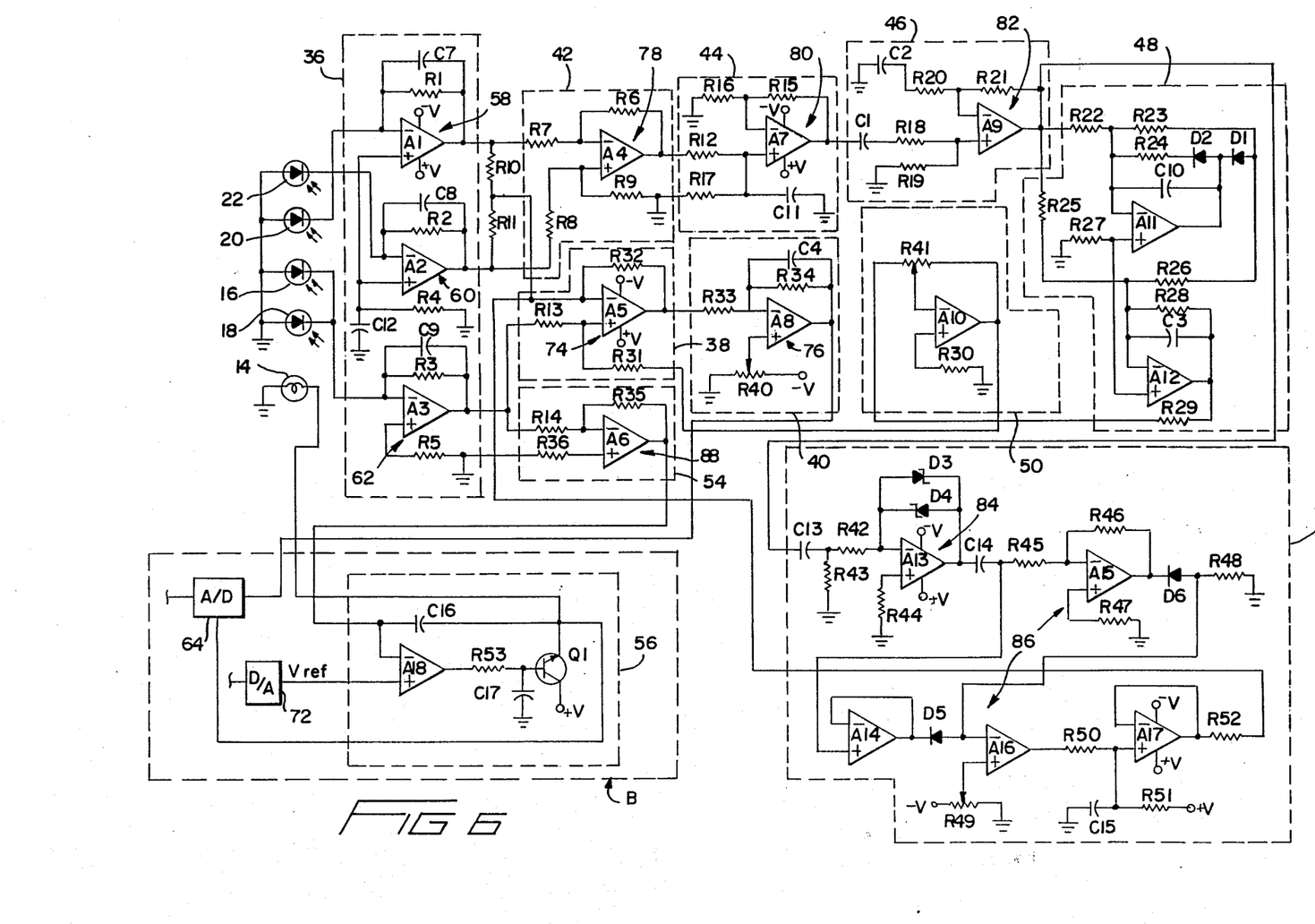
FIG. 6 is an electrical schematic diagram of the block diagram of FIG. 5.

The outputs of detectors 16, 18, 20 and 22 are amplified in circuit block 36 which comprises D.C. amplifier circuits 58, 60 and 62. Amplifier circuit 58 includes amplifier A1, resistor R1, capacitor C7 and supply voltage sources −V and +V. Amplifier circuit 60 includes amplifier A2, resistor R2 and capacitor C8. Amplifier circuit 62 includes amplifier A3, resistors R3 and R5 and capacitor C9. The non-inverting inputs of amplifiers A1 and A2 are grounded via a capacitor C12 in parallel with resistor R4. The non-inverting input of amplifier A3 is grounded via resistor R5.

Amplifier circuits 58, 60 and 62 are configured for short circuit operation of the detectors 16, 18, 20 and 22, to provide the most stable operation regarding temperature effects on the detectors 16, 18, 20 and 22, and to provide outputs which are proportional to the incident backscattered light on the detectors 16, 18, 20 and 22.

The outputs of measure detectors 20 and 22 are fed to amplifier circuits 58 and 60, respectively, and the output of reference detectors are combined and fed to amplifier circuit 62.

The outputs of measure detectors 20 and 22 are amplified and filtered in amplifier circuits 58 and 60, respectively, averaged through resistors R10 and R11 and then fed to circuit block 38. The output of reference detectors 16 and 18 are amplified and filtered in amplifier circuit 62 and fed to circuit block 38. The output of amplifier circuit 62 is maintained substantially constant by the automatic gain control circuit G, as will be described below.

CIRCUIT BLOCK 38

Circuit block 38 provides the consistency measurement of the stock slurry by comparing the difference voltage between the output of measure detectors 20 and 22 and the reference detectors 16 and 18. The difference voltage is amplified in amplifier circuit 74, which includes differential amplifier A5, resistors R13, R31 and R32 and supply voltage sources −V and +V. The output of circuit block 38 is preferably corrected to account for species type in the stock slurry—softwood or hardwood or a mixture of both—before the output is sent to the microprocessor console B. The outputs of compensation circuit F are preferably combined with the inputs to circuit block 38 to provide a consistency measurement signal which is insensitive to stock species or stock flow velocity. The outputs of compensation circuit F may alternatively be sent to the microprocessor console B where the necessary correction of the measurement signal of circuit block 38 may be performed.

CIRCUIT BLOCK 40

The output of circuit block 38 is fed to circuit block 40 which includes a "zero" bias amplifier circuit 76 to permit adjusting the output of circuit block 38 over a range of voltage to better accommodate the characteristics of microprocessor console B. The amplifier circuit 76 includes a differential amplifier A8, resistors R33 and R34, capacitor C4, potentiometer R40 and a voltage source −V. The non-inverting input of differential amplifier A8 is connected to the voltage source -V through the potentiometer R40.

SPECIES COMPENSATION

For a given consistency, a stock slurry of hardwood fibers will tend to provide a higher reading, since hardwood fibers exhibit more surface area than softwood fibers, and thus will tend to reflect more light into the first area 32 encompassing the reference detectors 16 and 18. Stock slurry of softwood fibers, on the other hand, will tend to provide a lower reading. This is clearly depicted in FIG. 10, where for a given consistency, hardwood registers a higher reading on the meter scale than softwood stock. Compensation of the output of measuring circuit E is therefore required to provide an accurate reading of the stock consistency.

Figure 8:
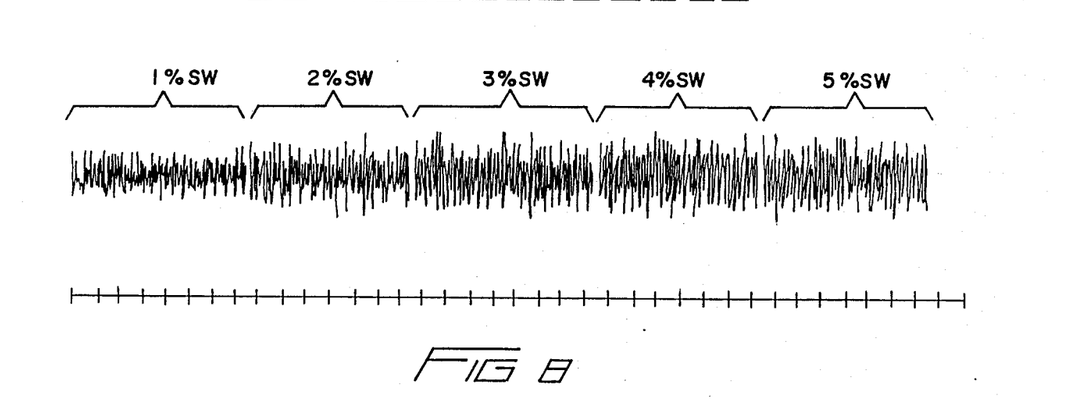
FIG. 8 and 9 are strip chart recordings of the output of photovoltaic measure detectors used in the present invention, for hardwood and softwood stock slurries for consistencies from 1% to 5%.
Figure 9:
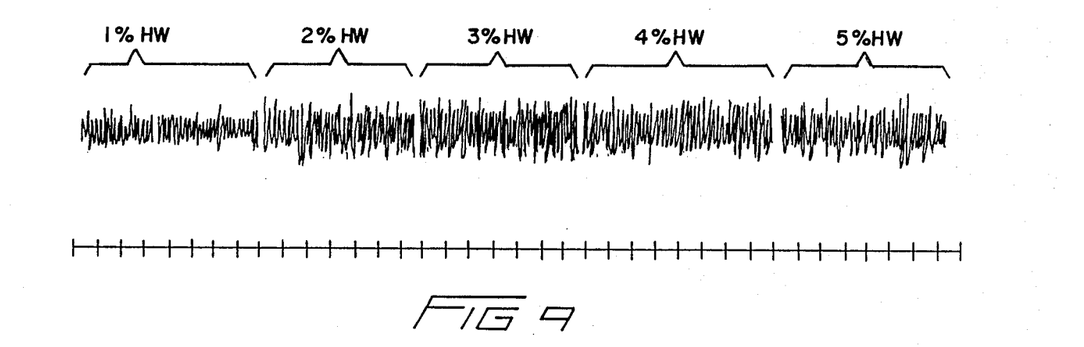

Species compensation is accomplished by differentially measuring the amplitude of the outputs of the measure detectors 20 and 22. The resulting signal, after further processing by compensation circuit F, is combined with the measurement circuit E to arrive at the compensated consistency measurement signal. The generated compensation signal for hardwood stock slurry is less than for softwood, as best shown in FIGS. 8 and 9, where the amplitude for hardwood is less than the amplitude for softwood. The signal level of the stock slurry, for constant consistency, diminishes with increase in surface area as occurs when measuring stock slurry of shorter length and smaller diameter, which is characteristic of hardwood fibers. The normal flocking tendency of the stock slurry is responsible for this phenomenon. Hardwood fibers generate a smaller amplitude and higher frequency signal than softwood for a given consistency and flow rate, since the flocking tendency for hardwood is one of causing smaller flocks, and thus a more homogenous suspension.

CIRCUIT BLOCK 42

The outputs of amplifier circuits 58 and 60 of circuit block 36 are fed to circuit block 42 which includes a differential amplifier circuit 78. The difference between the outputs of amplifier circuits 20 and 22 is amplified by differential amplifier circuit 78. The difference signal is characteristic of the species of the stock slurry, as described above. Amplifier circuit 78 includes differential amplifier A4, resistors R6, R7, R8 and R9.

CIRCUIT BLOCK 44

The output of circuit block 42 is further amplified in circuit block 44 which includes D.C. amplifier circuit 80. The high frequency A.C. component, including noise spikes, of the signal from circuit block 42 is attenuated by circuit block 44. Amplifier circuit 80 includes amplifier A7, resistors R12, R15, R16, and R17, capacitor C11, and supply voltage sources −V and +V.

CIRCUIT BLOCK 46

The output of circuit block 44 is fed to circuit block 46 which includes an A.C. amplifier circuit 82. The output of circuit block 46 is an amplified A.C. voltage of the differential output of measure detectors 20 and 22. Amplifier circuit 82 includes amplifier A9, resistors R18, R19, R20 and R21 and capacitors C1 and C2.

CIRCUIT BLOCK 48

The output of circuit block 46 is then rectified in circuit block 48 which provides peak-to-peak rectification. The output of circuit block 48 provides a varying D.C. voltage which is representative of the type of species of the stock slurry being measured, as best shown in FIGS. 8 and 9. Circuit block 48 includes amplifiers A11 and A12, resistors R22, R23, R24, R25, R26, R27, R28 and R29, capacitors C3 and C10, and diodes D1 and D2.

CIRCUIT BLOCK 50

Further amplification or attenuation is accomplished in circuit block 50, which is an adjustable gain D.C. amplifier circuit. Circuit block 50 includes a differential amplifier A10, potentiometer R41 and resistor R30. The output of circuit block 50 can be amplified or attenuated, depending on the calibration required to apply the appropriate amount of compensation to render the transmitter A species insensitive.

Finally, the output of circuit block 50 is combined with the inputs to circuit block 38 for species compensation.

The output of circuit block 50 may also be used to determine the ratio between softwood and hardwood fibers in a stock blend. By calibrating the output between 100% softwood and 100% hardwood for a given consistency, an output falling between the two extremes will indicate the ratio of hardwood to softwood by interpolation.

CIRCUIT BLOCK 52

Compensation circuit F also includes frequency/voltage converter circuit block 52 which generates a signal indicative of the stock flow velocity by measuring the frequency of the signal from the output of circuit block 46. The output of circuit block 46 is squared and then peak detected. The voltage present across capacitor C15 increases with an increase in signal frequency, such as occurs with an increase in flow rate. The flow signal is preferably fed to measurement circuit block 38 or sent to the microprocessor console B for error correction of the measurement caused by channeling of the stock slurry in front of window 26. Although the consistency measurement generally will not require flow velocity compensation, the flow rate signal is available for any purpose for process control.

Circuit block 52 includes a squaring circuit 84 and peak detecting circuit 86. The squaring circuit 84 includes amplifier A13, Zener diodes D3 and D4, resistors R42, R43 and R44, capacitors C13 and C14, and supply voltage sources −V and +V. The peak detecting circuit includes differential amplifiers A14, A15, A16 and A17, diodes D5 and D6, resistors R45, R46, R47, R48, R50, R51 and R52, potentiometer R49, capacitor C15 and voltage sources −V and V.

CIRCUIT BLOCK 54

Figure 7:
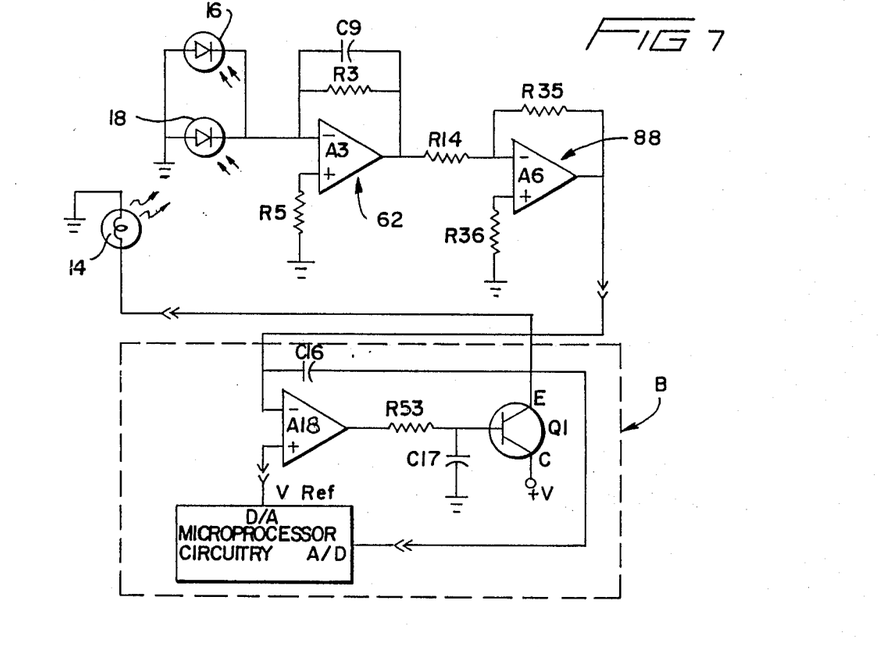
FIG. 7 is an electrical schematic diagram of an automatic gain control circuit used in the present invention.

The automatic gain control circuit G maintains the output of reference detectors 16 and 18 substantially constant. The combined output of reference detectors 16 and 18 is amplified and filtered in amplifier circuit 62 and further amplified in circuit block 54, which is a D.C. amplifier. Circuit block 54 includes amplifier A6 and resistors R14, R35 and R36.

CIRCUIT BLOCK 56

The output of circuit block 54 is compared to a reference voltage in circuit block 56, which includes an amplifier A18. The output of amplifier A18, which is the amplified difference between the reference voltage generated by the microprocessor console B and the output of amplifier circuit block 54, controls the voltage driving the lamp 14 through transistor Q1. Circuit block 56 increases the current to sufficiently drive the lamp 14. Circuit block 56 also continuously adjusts the voltage to the lamp 14 to cause the output current of reference detectors 16 and 18 to always be constant by means of the amplified signal from A6 equaling the V Ref. voltage. The V Ref. voltage is programmable through front panel display 70. The V Ref. voltage is adjustable to accommodate the desired voltage for the lamp 14.

Other components of circuit block 56 includes resistor R53, capacitors C16 and C17, and voltage source +V.

By employing the automatic gain control circuitry G to maintain the level of radiation incident on the reference detectors 16 and 18, errors due to variations in stock color, presence of "black liquor" in the stock water, degradation of lamp 14 and other effects which would normally decrease the detected radiation are minimized.

OPERATION In operation, the voltage reference is adjusted for the desired voltage for the lamp 14. Front panel display 70 inputs the reference voltage to the automatic gain control circuit G. Transmitter A is then calibrated against several stock slurries of known consistencies, e.g. 100% softwood and 100% hardwood, or customer's product, etc.. As a way of example only, the calibration may be done against 1%, 2%, 4% and 5% consistencies for 100% softwood and 100% hardwood. FIG. 10 shows an output of the transmitter A without species compensation and without linearization. The amount of species compensation is adjusted such that the output of the transmitter A is the same for softwood and hardwood for the same consistency. The output is then linearized in microprocessor console B so that readings between known points can be interpolated without calibrating the transmitter A against all consistencies. Thus, when the transmitter sends to the microprocessor console B an output which lies between, say between 1% and 2%, the microprocessor console B will interpolate the consistency based on the calibrated readings for 1% and 2% consistencies.

After calibration, the transmitter A is ready to measure the consistency of the stock slurry 4 and display the readings directly in the microprocessor console B.

The transmitter A may be installed in a consistency control loop, as best in FIG. 1, to automatically control the consistency of the stock slurry 4. Measurements by the transmitter A is analyzed by the microprocessor console relative to the desired consistency level. If the measured consistency is higher than the desired level, the microprocessor console B selectively opens the valve 5 to permit a measured amount of dilution water 3 to mix with the stock slurry 4, aided by the pump 11, thereby bringing the consistency down.

While this invention has been described as having preferred design, it is understood that it is capable of further modification, uses and/or adaptations of the invention following in general the principle of the invention and including such departures from the present disclosure as come within known or customary practice in the art to which the invention pertains, and as may be applied to the essential features set forth, and fall within the scope of the invention or the limits of the appended claims.

I claim:

1. An apparatus for determining the amount of particle suspension in a fluid by measuring radiation reflection on the particles, comprising:
   (a) means for producing a beam of radiation having at least first and second reflected portions;
   (b) means for directing said beam of radiation into the fluid;
   (c) first detector means for picking up at least said first portion of said beam of radiation reflected from the particle suspension in the fluid and for generating an output;
   (d) second detector means for picking up at least said second portion of said beam of radiation reflected from the particle suspension in the fluid and for generating an output;
   (e) said beam having sufficient power so as to penetrate the fluid a sufficient distance to cause said at least first and second reflected portions of said beam to reflect from the particle suspension and impinge on said first and second detectors means, respectively
   (f) means for maintaining substantially constant the output of said first detector;
   (g) said first and second detector means are disposed for permitting the output of said second detector means to increase relative to the output of said first detector means as the amount of particle suspension increases;
   (h) means for comparing the output of said second detector means relative to the output of said first detector means for obtaining the amount of particle suspension of the fluid; and
   (i) means for compensating the relative output between said first and second detector means for accounting for variations in surface areas of the particle suspension in the fluid.

2. An apparatus, as in claim 1, wherein:
   (a) said beam of radiation has an axial;
   (b) said first detector means is disposed within at least a portion of a first area defined by a first radius about the axis of said beam of radiation; and
   (c) said second detector means is disposed within at least a portion of a second area adjacent said first area, said second area being defined by a second radius about the axis of said beam and lying outside said first area.

3. An apparatus, in claim 2, wherein:
   (a) said first and second detector means are adjacent each other.

4. An apparatus, as in claim 2, wherein:
   (a) said first and second detector means are disposed on a plane.

5. An apparatus, as in claim 2, wherein:
   (a) said first and second detector means are each substantially transverse to the axis of said beam of radiation.

6. An apparatus, as in claim 1, wherein:
   (a) said means for directing said beam of radiation includes window means for permitting said beam of radiation to project into the fluid; and
   (b) said first and second detector means are adjacent said window means.

7. An apparatus, as in claim 6, wherein:
   (a) said window means includes an inner surface disposed away from the fluid; and
   (b) said first and second detector means are disposed on said inner surface.

8. An apparatus, as in claim 1, wherein:
   (a) said means for producing a beam of radiation includes an incandescent light source; and
   (b) said maintaining means includes means for keeping substantially constant the output current from said first detector means by varying the voltage across said light source.

9. An apparatus, as in claim 1, wherein:
   (a) each of said first and second detector means is a photovoltaic cell.

10. An apparatus, as in claim 1, wherein:
    (a) said comparing means includes a microprocessor console.

11. An apparatus, as in claim 10, wherein:
    (a) said microprocessor console includes means for converting the relative output of said first and second detector means to a linear output.

12. An apparatus as in claim 1, wherein:
    (a) said second detector means includes a pair of detectors; and (b) said compensating means includes means for generating a difference output from said pair of detectors.

13. An apparatus as in claim 12, wherein:
(a) said compensating means includes means for detecting the amplitude of the difference output of said pair of detectors.

14. An apparatus as in claim 13, wherein:
(a) said detecting means includes a peak to peak rectifier.

15. An apparatus as in claim 12, wherein:
(a) said generating means includes a differential amplifier operably connected to said pair of detectors.

16. An apparatus as in claim 1, wherein:
(a) said second detector means includes a pair of detectors operably connected to each other for providing a combined output; and
(b) means for generating a difference output from the combined output of said pair of detectors and said first detector means.

17. An apparatus as in claim 16, wherein:
(a) said comprising means includes a differential amplifier operably connected to the output of said compensating means and the combined output of said pair of detectors.

18. An apparatus for measuring the consistency of a flowing stock slurry containing radiation reflecting particles, comprising:
(a) means for producing a beam of radiation having at least first and second reflected portions;
(b) means for directing said beam of radiation into the stock slurry;
(c) first detector means for picking up at least said first portion of said beam of radiation reflected from the stock slurry and for generating an output;
(d) second detector means for picking up at least said portion of said beam of radiation reflected from the stock slurry for generating an output;
(e) said beam having sufficient power so as to penetrate the stock slurry a sufficient distance to cause said at least first and second reflected portions of said beam to reflect from the stock slurry and impinge on said first and second detectors;
(f) means for maintaining substantially constant the output of said first detector means;
(g) said first and second detector means are disposed for permitting the output of said second detector means to increase relative to the output of said first detector means as the consistency of the stock slurry increases;
(h) means for comparing the output of said second detector means relative to the output of said first detector means for obtaining the consistency of the stock slurry; and
(i) means for compensating the relative output between said first and second detector means for accounting for variations in surface areas of the particle suspension in the fluid.

19. An apparatus, as in claim 18, wherein:
(a) said means for directing said beam of radiation includes window means for permitting said beam of radiation to project into the stock slurry; and
(b) said window means is made of sapphire.

20. An apparatus as in claim 18, wherein:
(a) said second detector means includes a pair of detectors; and (b) said compensating means includes means for generating a difference output from said pair of detectors.

21. An apparatus as in claim 20, wherein:
(a) said compensating means includes means for detecting the amplitude of the difference output of said pair of detectors.

22. An apparatus as in claim 21, wherein:
(a) said generating means includes a differential amplifier operably connected to said pair of detectors.

23. An apparatus as in claim 18, and further comprising:
(a) means for compensating the relative output between said first and second detector means for accounting for the flow velocity of the fluid.

24. An apparatus as in claim 23, wherein:
(a) said second detector means includes a pair of detectors;
(b) means for generating a difference output from said pair of detectors;
said difference output includes frequency information; and
(d) means for converting said frequency information to a voltage which varies as the flow velocity of the fluid changes.

25. A method for determining the amount of particle suspension in a fluid by radiation reflection on the particles, comprising the steps of:
(a) projecting a beam of radiation into the fluid, said beam of radiation having at least first and second reflected portions;
(b) providing first and second detector means for picking up at least said first and second portions, respectively, of said beam of radiation reflected from the particle suspension in the fluid;
(c) maintaining substantially constant the output of said first detector means;
(d) positioning said first and second detector means such that the output of said second detector means increases relative to the output of said first detector means as the amount of particle suspension in the fluid increases;
(e) comparing the output of said second detector mean relative to said first detector means for obtaining the amount of particle suspension in the fluid; and
(f) compensating the relative output of said first and second detector means for accounting for variations in surface areas of the particle suspension in the fluid.

26. A method for maintaining the amount of particle suspension in a fluid to a desired level, comprising the steps of:
(a) projecting a beam of radiation into the fluid, said beam of radiation having at least first and second reflected portions;
(b) providing first and second detector means for picking up said at least first and second portions, respectively, of said beam of radiation reflected from the particle suspension in the fluid;
(c) maintaining substantially constant the output of said first detector means;
(d) positioning said first and second detector means such that the output of said second detector means increases relative to the output of said first detector means as the amount of particle suspension in the fluid increases;

(e) comparing the output of said second detector means relative to the output of said first detector means for obtaining the amount of particle suspension in the fluid.

(f) comparing the amount of particle suspension in the fluid against the desired level;

(g) compensating the relative output of said first and second detector means for accounting for variations in surface areas of the particle suspension in the fluid.

(h) increasing or decreasing the amount of particle suspension in the fluid to achieve the desired level and adding particles for increasing particle suspension and adding fluid for decreasing particle suspension;

(i) periodically monitoring the amount of particle suspension in the fluid;

(j) repeating said step of increasing or decreasing the amount of particle suspension in the fluid and said step of periodically monitoring the amount of particle as necessary.

27. A method, as in claim 26, and including the step of:

(a) continuously moving the particle suspension fluid past said beam of radiation.

28. A method for determining the flow velocity of a moving particle suspension in a fluid, comprising the steps of:

(a) projecting a beam of radiation into the fluid, said beam of radiation having at least first and second reflected portions;

(b) providing first and second detector means for picking up said at least first and second portions, respectively, of said beam of radiation reflected from the particle suspension in the fluid;

(c) providing a difference output from the outputs of said first and second detector means, said difference output having frequency which increases as the flow velocity of the fluid increases;

(d) converting the frequency of said difference output into a varying voltage which increases as the flow velocity of the fluid increases; and (e) correlating the varying voltage to the flow velocity of the fluid.

29. A method, as in claim 28, wherein:

(a) said step of converting includes the step of squaring and peak detecting said difference output.

* * * * *